United States Patent
Aeby et al.

(10) Patent No.: US 8,435,232 B2
(45) Date of Patent: May 7, 2013

(54) CATHETER HAVING TRI-AXIAL FORCE SENSOR

(76) Inventors: Nicolas Aeby, Geneva (CH); Giovanni Leo, Geneva (CH)

( * ) Notice: Subject to any disclaimer, the term of this patent is extended or adjusted under 35 U.S.C. 154(b) by 0 days.

(21) Appl. No.: 13/179,076

(22) Filed: Jul. 8, 2011

(65) Prior Publication Data
US 2011/0263934 A1 Oct. 27, 2011

Related U.S. Application Data

(62) Division of application No. 11/450,072, filed on Jun. 9, 2006, now Pat. No. 8,048,063.

(51) Int. Cl.
*A61B 19/22* (2006.01)
*G01L 1/24* (2006.01)

(52) U.S. Cl.
USPC ............. 606/1; 606/15; 606/41; 73/862.21; 73/862.624

(58) Field of Classification Search ......... 606/1, 7, 606/13–15, 41–50; 73/862.621, 862.624–862.629; 600/104, 485–488
See application file for complete search history.

(56) References Cited

U.S. PATENT DOCUMENTS

| | | |
|---|---|---|
| 4,757,194 A | 7/1988 | Simms |
| 4,873,989 A | 10/1989 | Einzig |
| 4,918,492 A | 4/1990 | Ferdinand et al. |
| 4,966,597 A | 10/1990 | Cosman |
| 4,983,034 A | 1/1991 | Spillman, Jr. |
| 5,014,709 A | 5/1991 | Bjelkhagen et al. |
| 5,018,529 A | 5/1991 | Tenerz et al. |
| 5,065,010 A | 11/1991 | Knute |
| 5,104,392 A | 4/1992 | Kittrell et al. |
| 5,122,137 A | 6/1992 | Lennox |
| 5,178,153 A | 1/1993 | Einzig |
| 5,201,317 A | 4/1993 | Kanazawa et al. |
| 5,202,939 A | 4/1993 | Belleville et al. |
| 5,279,793 A | 1/1994 | Glass |
| 5,289,256 A | 2/1994 | Gramling |
| 5,321,501 A | 6/1994 | Swanson et al. |
| 5,321,510 A | 6/1994 | Childers et al. |
| 5,348,019 A | 9/1994 | Sluss, Jr. et al. |

(Continued)

FOREIGN PATENT DOCUMENTS

| | | |
|---|---|---|
| DE | 30 20 785 | 12/1981 |
| DE | 38 28 550 | 3/1990 |

(Continued)

OTHER PUBLICATIONS

Application and File History for U.S. Appl. No. 12/127,657 filed May 27, 2008, inventor Leo.

(Continued)

*Primary Examiner* — Ahmed Farah
(74) *Attorney, Agent, or Firm* — Patterson Thuente Pedersen, P.A.

(57) ABSTRACT

A catheter for diagnosis or treatment of a vessel or organ is provided in which a flexible elongated body includes a tri-axial force sensor formed of a housing and a plurality of optical fibers associated with the housing that measure changes in the intensity of light reflected from the lateral surfaces of the housing resulting from deformation caused by forces applied to a distal extremity of the housing. A controller receives an output of the optical fibers and computes a multi-dimensional force vector corresponding to the contact force.

15 Claims, 2 Drawing Sheets

U.S. PATENT DOCUMENTS

| | | |
|---|---|---|
| 5,392,117 A | 2/1995 | Belleville et al. |
| 5,396,887 A | 3/1995 | Imran |
| 5,409,000 A | 4/1995 | Imran |
| 5,423,807 A | 6/1995 | Milder |
| 5,446,546 A | 8/1995 | Breidenbach et al. |
| 5,575,787 A | 11/1996 | Abela et al. |
| 5,594,819 A | 1/1997 | Narendran et al. |
| 5,633,494 A | 5/1997 | Danisch |
| 5,645,065 A | 7/1997 | Shapiro et al. |
| 5,662,108 A | 9/1997 | Budd et al. |
| 5,688,267 A | 11/1997 | Panescu et al. |
| 5,693,043 A | 12/1997 | Kittrell et al. |
| 5,696,863 A | 12/1997 | Kleinerman |
| 5,769,847 A | 6/1998 | Panescu et al. |
| 5,772,590 A | 6/1998 | Webster, Jr. |
| 5,782,828 A | 7/1998 | Chen et al. |
| 5,798,521 A | 8/1998 | Froggatt |
| 5,807,265 A | 9/1998 | Itoigawa et al. |
| 5,833,688 A | 11/1998 | Sieben et al. |
| 5,844,927 A | 12/1998 | Kringlebotn |
| 5,859,717 A | 1/1999 | Scobey et al. |
| 5,904,658 A | 5/1999 | Niederauer et al. |
| 5,906,614 A | 5/1999 | Stern et al. |
| 5,967,978 A | 10/1999 | Littmann et al. |
| 6,039,743 A | 3/2000 | Quiachon et al. |
| 6,056,436 A | 5/2000 | Sirkis et al. |
| 6,063,078 A | 5/2000 | Wittkampf |
| 6,066,130 A | 5/2000 | Gregory et al. |
| 6,088,088 A | 7/2000 | Fortenberry |
| 6,102,926 A | 8/2000 | Tartaglia et al. |
| 6,113,590 A | 9/2000 | Fischer et al. |
| 6,113,593 A | 9/2000 | Tu et al. |
| 6,120,476 A | 9/2000 | Fung et al. |
| 6,120,520 A | 9/2000 | Saadat et al. |
| 6,129,667 A | 10/2000 | Dumoulin et al. |
| 6,133,593 A | 10/2000 | Boos et al. |
| 6,134,003 A | 10/2000 | Tearney et al. |
| 6,171,275 B1 | 1/2001 | Webster, Jr. |
| 6,173,091 B1 | 1/2001 | Reich |
| 6,175,669 B1 | 1/2001 | Colston et al. |
| 6,197,023 B1 | 3/2001 | Muntermann |
| 6,210,346 B1 | 4/2001 | Hall et al. |
| 6,217,574 B1 | 4/2001 | Webster |
| 6,226,542 B1 | 5/2001 | Reisfeld |
| 6,226,551 B1 | 5/2001 | Zhu et al. |
| 6,246,898 B1 | 6/2001 | Vesely et al. |
| 6,256,090 B1 | 7/2001 | Chen et al. |
| 6,262,822 B1 | 7/2001 | Obhi et al. |
| 6,266,542 B1 | 7/2001 | Stern et al. |
| 6,266,551 B1 | 7/2001 | Osadchy et al. |
| 6,272,371 B1 | 8/2001 | Shlomo |
| 6,276,215 B1 | 8/2001 | Berg |
| 6,310,990 B1 | 10/2001 | Putnam et al. |
| 6,322,558 B1 | 11/2001 | Taylor et al. |
| 6,324,918 B1 | 12/2001 | Gitis et al. |
| 6,370,412 B1 | 4/2002 | Armoundas et al. |
| 6,398,778 B1 | 6/2002 | Gu et al. |
| 6,425,894 B1 | 7/2002 | Brucker et al. |
| 6,451,009 B1 | 9/2002 | Dasilva et al. |
| 6,458,123 B1 | 10/2002 | Brucker et al. |
| 6,466,811 B1 | 10/2002 | Hassett |
| 6,470,205 B2 | 10/2002 | Bosselmann et al. |
| 6,470,286 B1 | 10/2002 | Seip et al. |
| 6,471,710 B1 | 10/2002 | Bucholtz |
| 6,546,271 B1 | 4/2003 | Reisfeld |
| 6,547,780 B1 | 4/2003 | Sinofsky |
| 6,558,378 B2 | 5/2003 | Sherman et al. |
| 6,563,970 B1 | 5/2003 | Bohnert et al. |
| 6,572,804 B2 | 6/2003 | Randall et al. |
| 6,602,242 B1 | 8/2003 | Fung et al. |
| 6,660,001 B2 | 12/2003 | Gregory |
| 6,674,928 B2 | 1/2004 | Johnson et al. |
| 6,695,808 B2 | 2/2004 | Tom |
| 6,701,931 B2 | 3/2004 | Sliwa, Jr. et al. |
| 6,852,109 B2 | 2/2005 | Winston et al. |
| 6,868,195 B2 | 3/2005 | Fujita |
| 6,898,338 B2 | 5/2005 | Kersey et al. |
| 6,915,048 B2 | 7/2005 | Kersey et al. |
| 6,947,637 B2 | 9/2005 | Smith |
| 6,955,675 B2 | 10/2005 | Jain |
| 6,986,769 B2 | 1/2006 | Nelson et al. |
| 7,050,662 B2 * | 5/2006 | Behrmann et al. ............... 385/13 |
| 7,114,938 B2 | 10/2006 | Chou |
| 7,173,713 B2 | 2/2007 | Xu et al. |
| 7,241,986 B2 | 7/2007 | Wang |
| 7,460,964 B2 | 12/2008 | Mizota et al. |
| 7,466,879 B2 | 12/2008 | Tjin |
| 7,491,957 B2 * | 2/2009 | Kitamura et al. ........ 250/559.32 |
| 8,048,063 B2 | 11/2011 | Aeby et al. |
| 8,075,498 B2 | 12/2011 | Leo et al. |
| 8,157,789 B2 * | 4/2012 | Leo et al. ...................... 604/523 |
| 2001/0021843 A1 | 9/2001 | Bosselmann et al. |
| 2002/0041722 A1 | 4/2002 | Johnson et al. |
| 2002/0041723 A1 | 4/2002 | Ronnekleiv et al. |
| 2002/0057859 A1 | 5/2002 | Walter et al. |
| 2002/0072680 A1 | 6/2002 | Schock et al. |
| 2004/0082844 A1 | 4/2004 | Vardi et al. |
| 2004/0165810 A1 | 8/2004 | Fujita |
| 2004/0206365 A1 | 10/2004 | Knowlton |
| 2004/0243119 A1 | 12/2004 | Lane et al. |
| 2005/0062979 A1 | 3/2005 | Zhu et al. |
| 2005/0213870 A1 | 9/2005 | Kersey et al. |
| 2006/0013523 A1 | 1/2006 | Childlers et al. |
| 2006/0045408 A1 | 3/2006 | Jones et al. |
| 2006/0100610 A1 | 5/2006 | Wallace et al. |
| 2006/0133715 A1 | 6/2006 | Belleville et al. |
| 2006/0200049 A1 | 9/2006 | Leo et al. |
| 2006/0263002 A1 | 11/2006 | Pocha et al. |
| 2007/0014490 A1 | 1/2007 | Silverbrook et al. |
| 2007/0041019 A1 | 2/2007 | Schmidt |
| 2007/0043338 A1 | 2/2007 | Moll et al. |
| 2007/0060847 A1 | 3/2007 | Leo et al. |
| 2007/0065077 A1 | 3/2007 | Childers et al. |
| 2007/0151390 A1 | 7/2007 | Blumenkranz et al. |
| 2007/0151391 A1 | 7/2007 | Larkin et al. |
| 2007/0156019 A1 | 7/2007 | Larkin et al. |
| 2007/0265503 A1 | 11/2007 | Schlesinger et al. |
| 2008/0009750 A1 | 1/2008 | Aeby |
| 2008/0294144 A1 | 11/2008 | Leo et al. |
| 2009/0177095 A1 | 7/2009 | Aeby |
| 2009/0287092 A1 | 11/2009 | Leo et al. |
| 2009/0306643 A1 | 12/2009 | Pappone et al. |
| 2010/0063478 A1 | 3/2010 | Selkee |
| 2010/0087835 A1 | 4/2010 | Blumenkranz et al. |
| 2010/0094163 A1 | 4/2010 | Deladi et al. |
| 2010/0298826 A1 | 11/2010 | Leo et al. |
| 2010/0328675 A1 | 12/2010 | Bertholds et al. |
| 2011/0087112 A1 | 4/2011 | Leo et al. |
| 2012/0078138 A1 | 3/2012 | Leo et al. |

FOREIGN PATENT DOCUMENTS

| | | |
|---|---|---|
| EP | 0 281 405 | 9/1988 |
| EP | 0 934 728 | 8/1999 |
| EP | 1909650 | 4/2008 |
| EP | 2 047 797 | 4/2009 |
| JP | 09297078 | 11/1997 |
| JP | 10137200 | 5/1998 |
| JP | 2000227367 | 8/2000 |
| JP | 2004251779 | 9/2004 |
| WO | WO9729678 | 8/1997 |
| WO | WO 97/32182 | 9/1997 |
| WO | WO 97/38637 | 10/1997 |
| WO | WO 98/19044 | 5/1998 |
| WO | WO 99/45994 | 9/1999 |
| WO | WO 01/33165 | 5/2001 |
| WO | WO 01/74252 | 10/2001 |
| WO | WO 02/19898 | 3/2002 |
| WO | WO 02/19903 | 3/2002 |
| WO | WO 02/23148 | 3/2002 |
| WO | WO 02/47751 | 6/2002 |
| WO | WO2004/002303 | 1/2004 |
| WO | WO 2005/059510 | 6/2005 |
| WO | WO 2006/092707 | 9/2006 |
| WO | WO 2007/015139 | 2/2007 |
| WO | WO 2007/050960 | 5/2007 |
| WO | WO2007/109171 | 9/2007 |
| WO | WO 2007/111737 | 10/2007 |

| WO | WO 2008/000246 | 1/2008 |
| WO | WO 2008/003307 | 1/2008 |
| WO | WO 2008/045958 | 4/2008 |
| WO | WO 2009/114955 | 9/2009 |

OTHER PUBLICATIONS

Notice of Reasons for Rejection (translation) from Japanese Application No. 2007-557615 mailing date: Sep. 13, 2011.
International Preliminary Report on Patentability and Written Opinion from International Application No. PCT/IB2009/051967 date of issuance Nov. 17, 2010.
Application and File History for U.S. Appl. No. 11/237,053 filed Sep. 28, 2005, inventor Leo et al.
Application and File History for U.S. Appl. No. 11/450,072 filed Jun. 9, 2006, inventor Aeby.
Application and File History for U.S. Appl. No. 11/753,429 filed May 24, 2007, inventor Leo.
Application and File History for U.S. Appl. No. 12/352,426 filed Jan. 12, 2009, inventor Aeby.
Application and File History for U.S. Appl. No. 12/152,473 filed May 14, 2008, inventor Leo.
Application and File History for U.S. Appl. No. 13/096,647 filed Apr. 28, 2011, inventor Leo.
Application and File History for U.S. Appl. No. 11/436,926 filed May 15, 2006, inventor Leo.
Application and File History for U.S. Appl. No. 11/989,902 filed Feb. 1, 2008, inventor Leo.
Notification of the First Office Action for Chinese Application No. 20068007106.8 dated May 8, 2009.
Fernandez et al., "Multi-component force sensor based on multiplexed Fibre Bragg grating strain sensors" Measurement Science and Technology (2001) 810-813.
Paris-Seeley et al., "A compliance-independent pressure transducer for biomedical device-tissue interfaces," Biomed Instrum Technol. Nov.-Dec. 2000; 34(6): 423-31.
Brown, "Development of a Brillouin scattering based distributed fibre optic strain sensor," 2001.
Barrett, et al., "Extrinsic Fabry-Perot interferometer for measuring the stiffness of ciliary bundles on hair cells," Trans Biomed Eng. Mar. 1999; 46(3): 331-9.
Erdimer et al., "Fiberoptic measurement of tendon forces is influenced by skin movement artifact," J Biomech. Mar. 2003, 36(3): 449-55.
Schmidt et al., "Fiber-Optic Extrinsic Fabry-Perot Interferometer Strain Sensor with <50pm displacement resolution using three-wavelength digital phase demodulation," Optics Express, Apr. 9, 2001, vol. 8, No. 8.
"Fiber-optic strain-monitoring technology: BOTDR Brillouin Optical Time-domain Reflectometer," NTT Innovative Technology Site. Jul. 18, 2005.
Fearn et al., "An optical fiber transducer for single myofibril force measurement," Trans Biomed Eng. Nov. 1993; 40(11): 1127-32.
Komi et al., "Optic fibre as a transducer of tendomuscular forces," Eur J Appl Physiol 1996;72(3):278-80.
Del Villar et al., "Optimization of sensitivity in Long Period Fiber Gratings with overlay deposition," Optics Express, Jan. 10, 2005, vol. 13, No. 1.
Barb et al., "Versatile, high-speed force transducer using a laser fiode beam as an optical lever," J Appl Physiol 88: 308-314, 2000.
Rao, "Recent progress in applications of in-fibre Bragg grating sensors," Optics and Lasers in Engineering, vol. 31, Iss. 4, Apr. 1999, pp. 297-324.
Inaudi, "Application of optical fiber sensor in civil structural monitoring," The International Society for Optical Engineering, 2003.
Peirs et al., "Design of an Optical Force Sensor for Force Feedback during Minimally Invasive Robotic Surgery" 2003. Katholieke Univ. Leuven Belgium.
Zhang et al., "On SDM/WDM FBG Sensor Net for Shape Detection of Endoscope," Proceedings of the IEEE International Conference on Mechatronics & Automation, Jul. 2005.
Park et al, Force Sensing Robot Fingers using Embedded Fiber Bragg Grating Sensors and Shape Deposition Manufacturing. Santa Clara, CA 2007.
Endosense receives CE mark for Tacticath force-sensing ablation catheter, May 4, 2009.
Endosense launches TOCCATA clinical study Oct. 7, 2008.
"Endosense achieves ISO 13485 certification" Aug. 12, 2008.
"Endosense unveils five groundbreaking abstracts on contact force measurement for catheter ablation" May 13, 2008.
Fuster et al., "ACC/AHA/ESC 2006 Guidelines for the Management of Patients with Atrial Fibrillation," Circulation Journal of the Americal Heart Association, 2006, Dallas, Texas, pp. e319-e321.
Calkins et al., "HRS/EHRA/ECAS Expert Consensus Statement on Catheter and Surgical Ablation of Atrial Fibrillation: Recommendations for Personnel, Policy, Procedures and Follow-Up," Europace (2007).
Natale et al., "Venice Chart Internatinoal Consensus Document on Atrial Fibrillation Ablation," Journal of Cardiovascular Electrophysiology, vol. 18. No. 5, May 2007.
Cappato et al., "Worldwide Survey on the Methods, Efficacy, and Safety of Catheter Ablation for Human Atrial Fibrillation," Journal of the Americal Heart Association, 2005.
Hasin et al., "Miniature Force Transducer for Myocardial Stimulation and Local Tension Measurements," IEEE Transactions on Biomedical Engineering, vol. BME-26, No. 2, Feb. 1979.
"Sensei X Robotic Catheter System for Electrophysiology Procedures," MedGadget, Sep. 18, 2009.
"Intellisense Fine Force Technology," Hansen Medical (website), http://www.hansenmedical.com/products/intellisense.aspx Sep. 22, 1999.
Hansen Medical product brochure, Sensie Robotic Catheter System. 2009.
Hansen Medical product brochure, Artisan extend Control Catheter. 2009.
Peirs et al., "A micro optical force sensor for force feedback during minimally invasive robotic surgery," Sensors and Actuators A 115 (2004) 447-455.
Xiao et al., "Fiber optic pressure sensor with self-compensation capability for harsh environment applications," Optical Engineering May 2005, vol. 44(5).
European Office Action for European Application No. 06795186.3 dated Nov. 25, 2010.
European Office Action for European Application No. 06710474.5 dated Feb. 16, 2009.
European Office Action for European Application No. 06710474.5 dated Aug. 24, 2009.
International Search Report (PCT/IB2009/051967), dated Mar. 16, 2010.
Written Opinion and International Preliminary Report (PCT/IB2008/002675), dated Dec. 3, 2009.
International Search Report (PCT/IB2010/000021), dated May 27, 2010.
FISO, "FOS-N Strain Sensor," FISO Technologies Inc., (2006), Canada.
Dickmann, "Experiment 03, Fabry Perot Resonator," (2003), pp. 1-19.
Precision Photonics Corporation, "Basic Physics and Design of Etalons," (2003), pp. 1-5.
Luna Innovations, "EFPI Techniques for Strain and Displacement Sensing," (Aug. 1999).
Luna Innovations, "Fiber Optic Bragg Grating Sensor," www.lunainnovations.com/products/shape.asp, (Aug. 2005).
Meller, "Extrinsic Fabry-Perot Interferometer System Using Wavelength Modulated Source," (Dec. 1996).
FISO Technologies, "Technical Note, Principle of Fiber-Optic Sensors," (received prior to Feb. 20, 2007).
Uffelen, "Anchoring points for fibre optic strain sensors," Optical Techniques for Smart Structures and Structural Monitoring, (Feb. 1997), London, UK.
Lo, "Using in-fiber Bragg-grating sensors for measuring axial strain and temperature simultaneously on surfaces of structures," Optical Engineering, (Aug. 1998) vol. 37, Issue 8, pp. 2272-2276.

Dupont, "DuPont Zenite LCP liquid crystal polymer resin," Product and Property Guide, K-15415, May 2006.

Yokoyama, MD, et al., "Novel Radiofrequency Ablation Catheter with Contact Force Sensor Predicts Lesion Size and Incidence of Steam Pop in Canine Model," Heart Rhythm Society, May 2007, Denver USA, vol. 4, Issue 5.

Shah et al., "Evaluation of a New Catheter Sensor for Real-Time Measurement of Tissue Contact," Heart Rhythm Society, May 2006, Boston, USA, vol. 3, Issue 5.

"The Unique Force Sensor Ablation Catheter," www.endosense.com/site/product.htm, Mar. 2007.

European Office Action from European Application No. 06795186.3 dated Aug. 9, 2011.

European Office Action from European Application No. 11158967.7 dated Aug. 10, 2011.

Application and File History for U.S. Appl. No. 13/308,196, filed Nov. 30, 2011, inventors Leo et al.

Application and File History for U.S. Appl. No. 13/447,813, filed Apr. 16, 2012, inventors Leo et al.

European Office Action for European Application No. 08826173.0-1265 dated Oct. 1, 2012.

European Office Action for European Application No. 06795186.3-2310 dated Oct. 18, 2012.

Notification of the First Office Action of Chinese Office Action for Chinese Application No. 200980125027.0 dated Jun. 29, 2012.

European Office Action from European Application No. 09746251.9 dated Jan. 24, 2012.

* cited by examiner

CATHETER HAVING TRI-AXIAL FORCE SENSOR

RELATED APPLICATION

The present application is a divisional of U.S. patent application Ser. No. 11/450,072, filed Jun. 9, 2006.

FIELD OF THE INVENTION

The present invention relates to a catheter for exploring and treating a vessel or a bodily organ that permits the detection and computation of the contact forces between a sensor affixed to an extremity of the catheter and a wall of the vessel or organ.

BACKGROUND OF THE INVENTION

Catheter-based diagnostic and treatment systems have made possible the exploration and treatment of various bodily vessels and organs. Such catheters are introduced through a vessel leading to the cavity in the target organ, or may alternatively be introduced directly into the organ through an incision made in the wall of the organ. These procedures avoid the trauma to the patient and the extended recuperation times typically associated with an open surgical procedure.

To provide effective diagnosis or therapy, it is frequently necessary to first map the zone to be treated with great precision. Such mapping may be performed, for example, when it is desired to selectively ablate current pathways within a heart to treat atrial fibrillation. Often, the mapping procedure is complicated by difficulties in locating the zone(s) to be treated because of the periodic movements of the heart throughout the cardiac cycle.

Previously-known systems for mapping the interior of a vessel or organ are described, for example, in U.S. Pat. Nos. 6,546,271 and 6,226,542. The catheters described in those patents employ electro-magnetic, magnetic or acoustic sensors to map the position of a distal end of the catheter in space and then construct a three-dimensional visualization of the vessel or organ interior.

One drawback of such previously known mapping systems is that they require manual feedback from the catheter and/or impedance measurements to determine when the catheter is properly positioned relative to the wall of the vessel or organ. Those previously-known systems do not measure contact forces with the vessel or organ wall nor do they detect contact forces applied by the catheter against the organ or vessel wall, which may modify the true location of the wall. Instead, previously known mapping methods are time-consuming, highly dependent upon the skill of the clinician, and are unable to compensate for artifacts created by excessive contact forces.

It therefore would be desirable to provide apparatus and methods for detecting and monitoring contact forces between a mapping catheter and the wall of an organ or vessel, so to enable faster and more accurate mapping. It also would be desirable to provide apparatus and methods that permit the process to be automated, thereby improving registration of measured electro-physiologic values and spatial coordinates, for example, by recording such values only where the contact forces fall within a predetermined range.

Once the topography of the vessel or organ is mapped, either the same or a different catheter may be employed to effect treatment. Depending upon the specific treatment to be applied to the vessel or organ, the catheter may comprise any of a number of end effectors, such as radio frequency ablation electrodes, a rotary cutting head, laser ablation system, injection needle or cryogenic fluid delivery system. Exemplary systems are described, for example, in U.S. Pat. Nos. 6,120,520, 6,102,926, 5,575,787, 5,409,000 and 5,423,807.

Because the effectiveness of such end effectors often depends on having the end effector in contact with the wall of the organ or vessel, many previously-known treatment systems include expandable baskets or hooks that stabilize the extremity of the catheter in contact with the wall. Such arrangements, however, may be inherently imprecise due to the motion of the organ or vessel. Moreover, the previously-known systems do not provide the ability of sense the load applied to the distal extremity of the catheter by movement of the tissue wall.

For example, in the case of a cardiac ablation system, at one extreme the creation of a gap between the end effector of the treatment system and the tissue wall may render the treatment ineffective and inadequately ablate the tissue zone. At the other extreme, if the end effector of the catheter contacts the tissue wall with excessive force, if may inadvertently puncture the tissue, resulting in cardiac tamponade.

In view of the foregoing, it would be desirable to provide a catheter-based diagnostic or treatment system that permits sensing of the load applied to the distal extremity of the catheter, including periodic loads arising from movement of the organ or tissue. It further would be desirable to have a load sensing system coupled to control operation of the end effector, so that the end effector is operated, either manually or automatically, only when the contact force is detected to fall within a predetermined range.

U.S. Pat. No. 6,695,808 proposes several solutions to measure the force vector arising from contact with a tissue surface, including mechanical, capacitive, inductive and resistive pressure sensing devices. One drawback of such devices, however, is that they are relatively complex and must be sealed to prevent blood or other liquids from disturbing the measurements. In addition, such load sensing devices may result in an increase in the insertion profile of the distal extremity of the catheter. Still further, sensors of the types described in that patent may be subject to electromagnetic interference.

One previously-known solution for dealing with potential electromagnetic interference in the medical environment is to use light-based systems rather than electrical measurement systems, such as described in U.S. Pat. No. 6,470,205 to Bosselman. That patent describes a robotic system for performing surgery comprising a series of rigid links coupled by articulated joints. A plurality of Bragg gratings are disposed at the articulated joints so that the bend angle of each joint may be determined optically, for example, by measuring the change in the wavelength of light reflected by the Bragg gratings using an interferometer. Calculation of the bend angles does not require knowledge of the characteristics of the rigid links.

International Publication No. WO 01/33165 to Bucholtz describes an alternative spatial orientation system wherein wavelength changes measured in a triad of optical fiber strain sensors are used to compute the spatial orientation of a catheter or other medical instrument.

An article by J. Peirs et al., entitled "Design of an Optical Force Sensor for Force Feedback during Minimally Invasive Robotic Surgery," published by Katholieke Universiteit Leuven, Belgium, describes a tri-axial force sensor for use generating force feedback systems in a robotic surgery system. The apparatus includes a plurality of optical fibers that direct light onto a mirrored surface disposed adjacent to a distal tip of the device. The intensity of the light reflected from the mirrored surface is measured and may be correlated to the force required to impose a predetermined amount of flexure to the distal tip. The article describes a flexible and compact structure that supports the mirrored surface and produces variations in light intensity responsive to contact forces that deform the structure.

In view of the drawbacks of the previously known catheters, it would be desirable to provide diagnostic and treatment apparatus, such as a catheter, that permits sensing of loads applied to a distal extremity of the apparatus, but which do not substantially increase the insertion profile of the apparatus.

It further would be desirable to provide diagnostic and treatment apparatus, such as a catheter, that permits the computation of forces applied to a distal extremity of the apparatus, and which is substantially immune to electromagnetic interference.

It also would be desirable to provide a catheter having force-sensing capability that includes a compact and flexible force measurement structure that may be used to modulate reflected light intensities responsive to contact forces arising from contact between a distal end of the catheter and a target organ or vessel.

SUMMARY OF THE INVENTION

In view of the foregoing, it is an object of the present invention to provide a diagnostic or treatment catheter that permits a tri-axial sensing of the forces applied to an extremity of the catheter, including periodic loads arising from movements of the organ or tissue.

It is another object of this invention to provide a catheter for detecting and monitoring contact forces between the catheter and the wall of an organ or vessel, to facilitate the speed and accuracy of such mapping.

It is a further object of the present invention to provide a catheter having a load sensing system coupled to an end effector of a diagnostic or treatment catheter, so that the end effector is operated, either manually or automatically, only when the contact force is detected to fall within a predetermined range.

It is also an object of this invention to provide a diagnostic and treatment catheter that permits sensing of loads applied to an extremity of the catheter, but which do not substantially increase the insertion profile of the apparatus.

It is yet another object of the present invention to provide a catheter for use in a hollow-body organ, such as the heart, that permit sensing of loads applied to an extremity of the catheter during movement of the organ, so as to optimize operation of an end effector disposed within the distal extremity.

It is a further object of this invention to provide a catheter having force-sensing capability that includes a compact and flexible force measurement structure that may be used to modulate reflected light intensities responsive to contact forces arising from contact between a distal end of the catheter and a target organ or vessel.

These and other objects of the present invention are accomplished by providing a catheter comprising a flexible elongated body and a tri-axial force sensor affixed to an extremity of the flexible elongated body. The tri-axial force sensor includes a housing having a plurality of mirrored surfaces and optical fibers associated therewith. The optical fibers are disposed relative to the housing to detect light intensity changes resulting from longitudinal and radial deformations of the housing. A controller is provided to compute a force vector responsive to-detected light intensity changes.

In one embodiment, the housing comprises a plurality of columnar members narrowly spaced from each other and extending longitudinally between a proximal ring and a distal ring. Preferably, the columnar members are spaced equi-distant around the longitudinal axis and define a parallelogram-shaped structure. Each columnar structure preferably includes a pair of longitudinal beams that are substantially parallel and joined to a pair of lateral beams that are also substantially parallel.

One of the longitudinal beams extends longitudinally to join the parallelogram-shaped structure to the proximal ring and an opposite longitudinal beam also extends longitudinally to join the parallelogram-shaped structure to the distal ring. Preferably, the longitudinal beams have a larger cross-section than the lateral beams. The housing additionally may comprise mating tongue-and-groove indentations between neighboring longitudinal beams to protect the optical fibers from axial overload.

The tri-axial forces sensor further comprises a reflective surface disposed within the housing that reflects differing amounts of light to the optical fibers responsive to the contact forces applied to the housing. In a preferred embodiment, at least one of the optical fibers is disposed so as to detect a variation in reflected light intensity due to a change in the size of a gap between two columnar members, and at least one of the optical fibers is disposed to detect a variation in reflected light intensity due to a change in the size of a gap between a lateral beam and a proximal or distal ring. Preferably, two of the optical fibers are spaced equi-distant apart around the circumference of the housing, e.g., 90 degrees or 120 degrees.

The extremely small dimensions of the optical fibers and compact design of the housing provide ample space in the distal extremity of the catheter to house one or more end effectors for other diagnostic or treatment purposes, for example, an electrode to measure an electric potential (e.g., to perform an endocavity electrocardiogram), an electrode configured to ablate tissue by deposition of radiofrequency energy, an irrigation channel, and/or a three-dimensional positioning sensor.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE DRAWINGS

The present invention is directed to a catheter for the diagnosis and treatment of a bodily vessel or organ, in situations where it is desired to detect and measure contact forces between a distal extremity of the catheter and a wall of the organ or vessel. The force sensing capability of the catheter may be used intermittently to measure the contact forces at discrete points, or alternatively, used to continuously monitor contact forces to assist in the manipulation and operation of the device.

In a preferred embodiment, the catheter of the present invention may be manually operated by a clinician and employs a visual or audio cue generated by the output of the tri-axial force sensor so to determine, e.g., an optimum position for measuring an electro-physiologic value or for performing a treatment. Advantageously, a catheter equipped with the force sensing system of the present invention is expected to permit faster, more accurate diagnosis or treatment of a vessel or organ, with improved registration between spatial locations and applied pressures.

For example, a catheter having the inventive force measuring capability would enable the application of adequate pressure against a tissue or an organ without perforating or damaging the tissue or organ because of the clinician's lack of tactile response to the applied pressure. This causes the results of the insertion process to be less dependent on the skill of the individual clinician and facilitates automated procedures.

Figure 1:
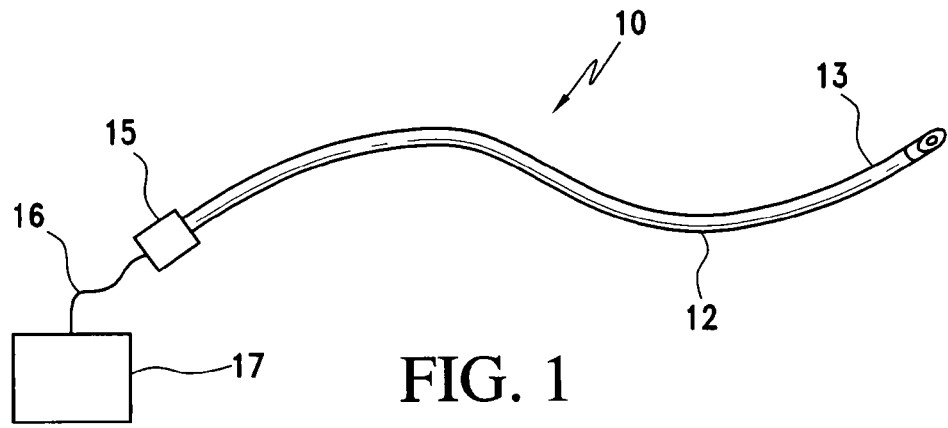
FIG. 1 is a schematic view of an apparatus constructed in accordance with the principles of the invention.
Figure 2:
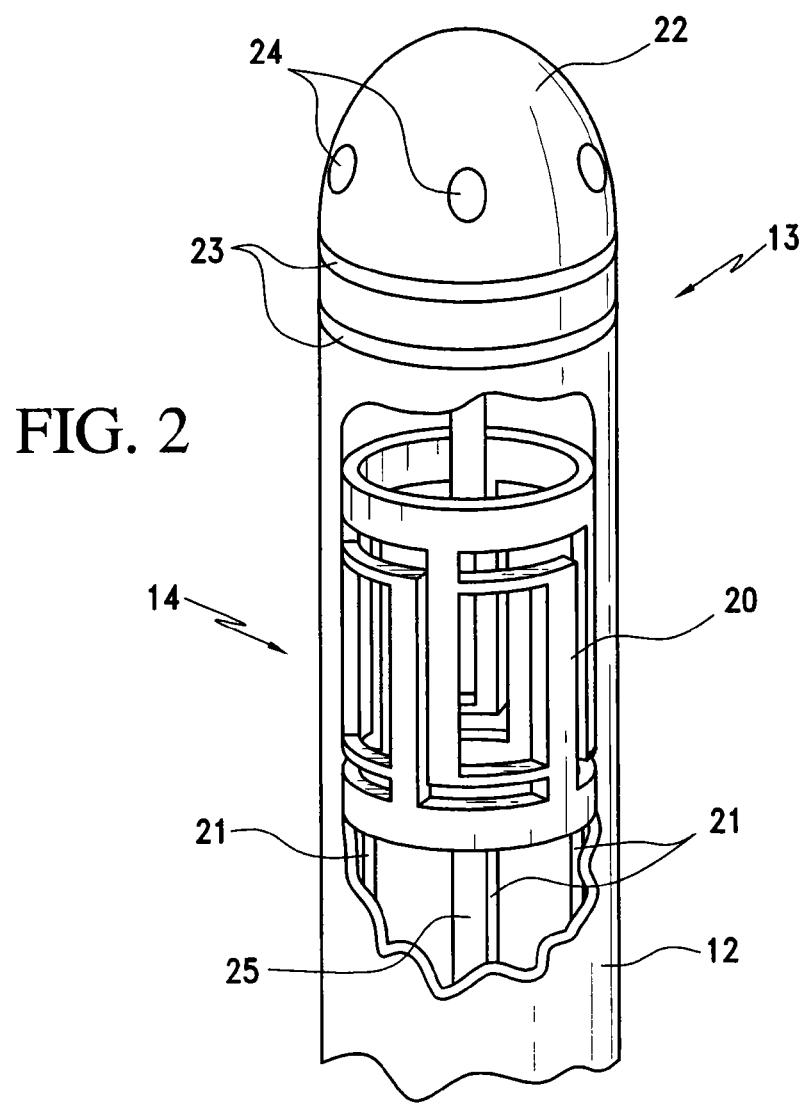
FIG. 2 is a perspective cutaway view of the distal extremity of the catheter of FIG. 1.

Referring to FIGS. 1 and 2, a catheter embodying the tri-axial force sensing system of the present invention is described. Catheter 10 comprises flexible elongated body 12, of a length and a width suitable for insertion into a bodily vessel or organ, having distal extremity 13 including tri-axial force sensor 14. Tri-axial force sensor 14 is configured to detect changes in light intensity caused by forces applied to distal extremity 13, e.g., when distal extremity 13 contacts the wall of a bodily vessel or organ. Distal extremity 13 may further include one or more end effectors, e.g., mapping electrodes or ablation electrodes, such as are known in the art for diagnosis or treatment of a vessel or organ. Catheter 10 is coupled at proximal end 15 via cable 16 to controller 17, which may include a microprocessor, and receives and processes signals from tri-axial sensor 14 to compute a contact force vector.

In one preferred application, catheter 10 is configured as an electrophysiology catheter for performing cardiac mapping and ablation. In other embodiments, the catheter may be configured to deliver drugs or bioactive agents to a vessel or organ wall or to perform minimally invasive procedures such as transmyocardial revascularization or cryo-ablation.

Referring now also to FIG. 3, distal extremity 13 of an electrophysiology embodiment of catheter 10 is described. Distal extremity 13 includes tri-axial force sensor 14 comprising housing 20 and plurality of optical fibers 21 that extend through flexible elongated body 12. Distal extremity 13 further includes RF ablation electrode 22, plurality of mapping electrodes 23 and irrigation ports 24. Irrigation ports 24 are coupled to proximal end 15 of catheter 10 via irrigation tube 25. Distal extremity 13 also may include a pull wire- or other mechanism for selectively deflecting the ablation electrode at locations distally of the tri-axial force sensor.

The distal ends of optical fibers 21 are disposed relative to the housing 20 to emit light onto reflective surfaces of housing 20 and to collect light reflected from those surfaces. Optical fibers 21 may be arranged in pairs, with one optical fiber coupled to an emitter, e.g., a light source such as a LED or a tunable laser diode, and another optical fiber coupled to a receiver, e.g., a photodiode, to generate a signal corresponding to the intensity of the reflected light. The emitters and receivers for each pair of optical fibers may be located either in proximal portion 15 of the catheter or controller 17. Alternatively, the emitter and receiver may be optically coupled to a single optical fiber disposed in catheter 10 via a suitable optocoupler, thereby reducing the number of optical fibers extending through flexible elongated body 12.

Still referring to FIG. 3, housing 20 preferably is configured to decouple the axial and radial deformations arising from application of a contact force to distal extremity. This is expected to overcome the drawback of previously known flexible catheter ends, in which torque caused by radial forces typically generates larger deformations than axial forces of the same magnitude. In a preferred embodiment, housing 26 provides sensitivity of roughly the same order of magnitude for longitudinal and radial forces, as described below.

Figure 3A:
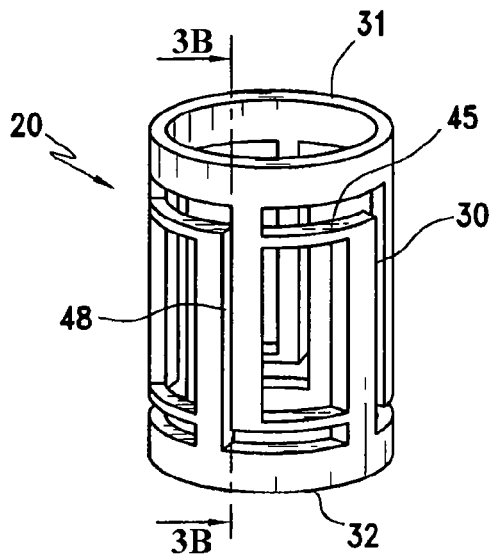
FIGS. 3A and 3B are, respectively, perspective and plan, expanded views of the housing of a tri-axial force sensor.
Figure 3B:
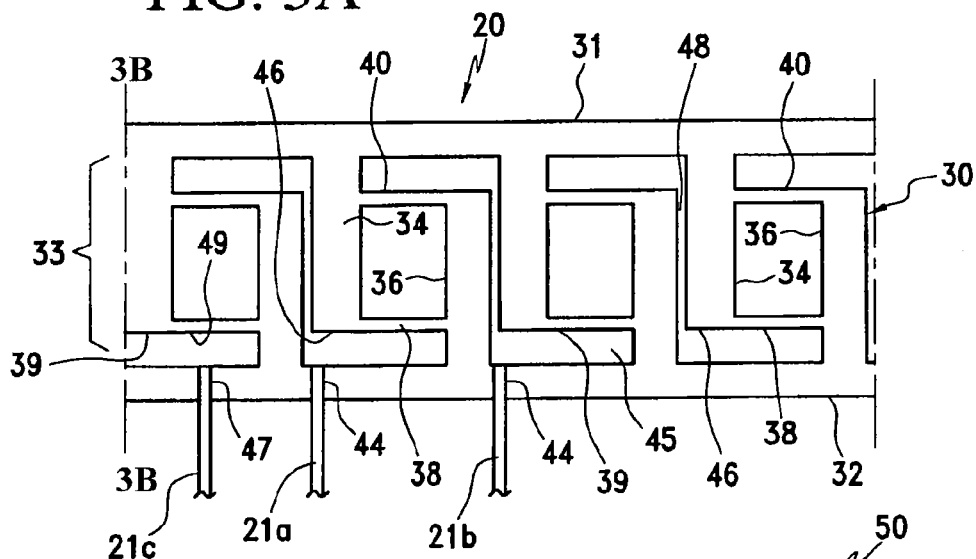

In FIG. 3A housing 20 is shown in perspective view, while in FIG. 3B the housing is shown cut along line 3B-3B in FIG. 3A and flattened. In accordance with one aspect of the present invention, decoupling of the axial and radial deformations of housing 20 is achieved by providing a structure that comprises plurality of columnar members 30 separated by narrow longitudinal gaps. Columnar members 30 preferably are disposed symmetrically around the longitudinal axis of housing 20 and can be in any number, preferably between two and six, and more preferably three or four.

Columnar members 30 extend between distal ring 31 and proximal ring 32, and each have parallelogram-shaped structure 33. Each parallelogram structure 33 comprises two substantially parallel longitudinal beams 34 and 36 and two substantially parallel lateral beams 38 and 40. The connection of columnar members 30 to distal and proximal rings 31 and 32, respectively, is provided by having longitudinal beam 34 extend to connect to distal ring 31, and longitudinal beam 36 extend to connect to proximal ring 32.

Columnar members 30 are arranged so that when closed to form a circular cylinder, as in FIG. 3A, adjacent longitudinal beams 34 (or 36) are separated around the circumference of housing 20 by 90.degree. to 120.degree. The lower surface 39 of each of lateral beam 38 is coated with a reflective surface. Optical fibers 21a and 21b extend through apertures 44 in proximal ring 32 so that light conducted through the optical fibers is emitted into gaps 45 and impinges upon the reflective surfaces of lateral beams 38 at free edges 46, which preferably are spaced 90.degree. to 120.degree. apart around the circumference of the housing.

Optical fiber 21c likewise extends through aperture 47 so that light is emitted into gap 48 and impinges upon the reflective surface of mid-span 49 of another of lateral beams 38. Optical fibers 21a-21c collect light reflected from free edges 46 and mid-span 49, and provide signals corresponding to the intensity of light reflected from those surfaces to controller 17 for processing, as described below.

Figure 4:
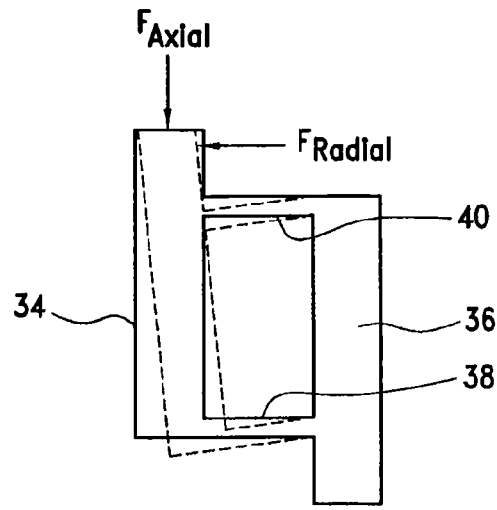
FIG. 4 is a schematic view illustrating deformation of a columnar member of the housing of FIG. 3 during loading.

The mode of deformation of columnar members 30 is depicted in FIG. 4. Upon the imposition of axial contact force $F_{axial}$, longitudinal beams 34 are displaced longitudinally without deformation, while lateral beams 38 and 40 deflect elastically downwards, thereby reducing the size of gaps 45 between lateral beam 38 and proximal ring 32. Light reflected to optical fiber 21c will increase in intensity as gap 45 reduces, which reduction in gap may be empirically correlated to the applied axial force.

Likewise, when radial force $F_{radial}$ is applied to columnar member 30, longitudinal beams 34 and 36 deflect elastically towards or away from one another, while lateral beams 38 and 40 remain essentially underformed. This movement of longitudinal beams 34 and 36 will reduce or increase the size of gaps 48 between longitudinal beams 34 and 36 of adjacent columnar members 30. Consequently, light reflected to optical fibers 21a and 21b, positioned to collect light reflected from free edges 46 of adjacent columnar members 30, will increase or decrease in intensity as gaps 48 change size. The change in gap size 48 also may be empirically correlated to the applied radial force, so that a given change in reflected light detected by optical fibers 21a and 21b may be used to compute an applied radial force.

In view of the foregoing, it will be understood that when a force having both radial and axial components is applied to housing 20, columnar members 30 will experience both longitudinal and radial displacement, as depicted in FIG. 4. Based upon the resulting changes in the sizes of gaps 45 and 48, as determined by changes in the intensity of the reflected light, controller 17 will compute the axial and radial components of the applied force. Moreover, because optical fibers 21a and 21b detect deformations of columnar members that are spaced 90.degree. apart around the circumference of the housing, controller 17 also may be programmed to compute the sense (i.e., direction) of the applied force.

In a preferred embodiment, gaps 45 and 48 typically are less than 100 .mu.m. For example, for a housing having a length of 8.85 mm, an outer diameter of 5 mm and a wall thickness of 0.5 mm for the columnar member, gaps 45 and 48 may be in a range of approximately 50 .mu.m to 100 .mu.m, and may have a usable range of applied axial and radial forces from about 0.1 N to 5 N.

As described above, housing 20 of the tri-axial force sensor of the present invention is configured to decompose contact forces applied to distal extremity 13 of catheter 10 into radial and axial components that result in deflections of the longitudinal and lateral beams of the columnar members. These deflections, which are detected based upon changes in the intensity of reflected light collected by optical fibers 21a-21c, may then be used by controller 17 to determine the contact force applied to the distal extremity.

In a preferred embodiment, controller 17 is preprogrammed or uses catheter-specific algorithms or look-up tables to convert the light intensity changes to corresponding force components. Controller 17 further may be programmed to use these force components to compute a multi-dimensional force vector quantifying the contact force. The resulting force vector then may be displayed in real-time in any of a variety of formats, useful to the clinician, on a display screen associated with controller 17.

For example, controller 17 may provide the values for the measured contact forces as numerical values that are displayed on a screen associated with controller 17. Alternatively or in addition, the display screen may include a graphic including a variable size or colored arrow that points at a position on the circumference of a circle to visualize the magnitude and direction of the transverse force applied to the distal extremity of the catheter. By monitoring this display, the clinician may continuously obtain feedback concerning the contact forces applied to distal extremity of the catheter.

Because the light intensity-force conversion table or algorithm may be housing specific, it is contemplated that it may be necessary to generate a catheter-specific table or algorithm during manufacture of the catheter. This information, which is then supplied to the controller when the catheter is used, may be stored with the catheter in the form of a memory chip, RFID tag or bar code label associated with the catheter or its packaging.

Figure 5:
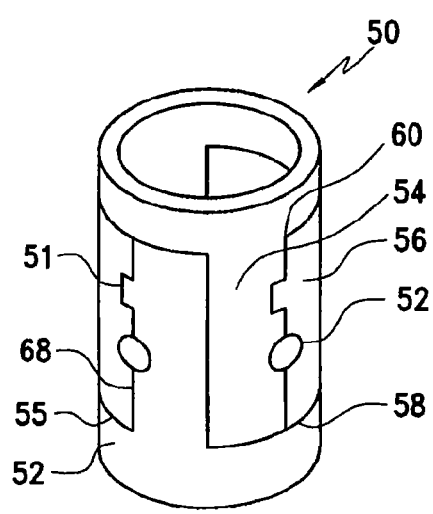
FIG. 5 is a perspective view of a manufacturable embodiment of a housing suitable for use in the tri-axial force sensor of the present invention.

Turning now to FIG. 5, an embodiment of a housing 50 suitable for use in the tri-axial force sensor of the present invention is described. Housing 50 is a manufacturable embodiment based upon the schematic representations of FIGS. 3 and 4, in which longitudinal beams 54 and 56 of FIG. 5 correspond to beams 34 and 36 of FIG. 3, lateral beams 58 and 60 of FIG. 5 correspond to lateral beams 38 and 40 of FIG. 3. In FIG. 5, gap 55 and longitudinal gap 68 correspond to gaps 45 and 48, respectively, of FIG. 3.

Housing 50 preferably is formed by laser cutting or electro-discharge machining ("EDM") a titanium alloy tube, such as Ti6Al4V, and includes stops 51, consisting of mating tongue-and-groove indentations sculpted in longitudinal gaps 68. Stops 51 limit axial deflections of the beams of housing 50 to prevent axial force overloads that could impose plastic strains and thus ruin the tri-axial sensor. Circular openings 52 may be provided as starting openings when using an EDM process to machine gaps 45 and 48, and various other slits. Housing 50 includes apertures (not shown) that permit placement of the optical fibers to measure light intensity changes resulting from deformation of the housing, as discussed above with respect to the embodiment of FIGS. 2-4.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

The invention claimed is:

1. An apparatus for exploration or treatment of a vessel or organ, the apparatus comprising:
   a flexible elongated body having a proximal end and a distal extremity, the distal extremity including an ablation end effector having irrigation ports;
   at least one irrigation channel disposed within the flexible elongated body, the at least one irrigation channel being in fluid communication with the irrigation ports;
   a flexible force measurement structure affixed to the distal extremity of the flexible elongate body, the flexible force measurement structure including a proximal ring and a distal ring arranged concentrically about a longitudinal axis, the flexible force measurement structure being operatively coupled with an emitter and a plurality of receivers, the plurality of receivers adapted to receive signals emitted from the emitter and, in response, the plurality of receivers adapted to output signals that vary in response to a displacement of the distal ring relative to the proximal ring due to a contact force on an exterior of the distal extremity of the flexible elongate body; and
   a controller including a microprocessor operatively coupled with the plurality of receivers and adapted to receive and process the signals output therefrom, the microprocessor being configured to compute a contact force vector from the signals, the contact force vector being multi-dimensional and corresponding to the contact force on the exterior of the distal extremity of the flexible elongate body.

2. The apparatus of claim 1, wherein the ablation end effector is a radiofrequency ablation electrode.

3. The apparatus of claim 1 wherein the plurality of receivers are fiber optics.

4. The apparatus of claim 3, wherein the emitter is a light source operatively coupled to the fiber optics.

5. The apparatus of claim 1, wherein the controller is configured to control operation of the ablation end effector based on the signals output from the plurality of receivers.

6. The apparatus of claim 5 wherein the controller is configured to operate the ablation end effector when a magnitude of the multi-dimensional force is within a predetermined range of values.

7. The apparatus of claim 1, wherein a direction of the multi-dimensional force vector ranges from a purely axial force to a purely radial force.

8. The apparatus of claim 1, wherein the emitter and at least one of the plurality of receivers are optically coupled to a single optical fiber disposed in the flexible elongate body.

9. The apparatus of claim 1 further comprising a plurality of columnar members extending longitudinally between the proximal ring and the distal ring, each of the columnar members defined by a pair of laterally-oriented members coupled to a pair of longitudinally oriented members.

10. The apparatus of claim 9 wherein the pair of laterally-oriented members is coupled to the pair of longitudinally-oriented members to form a parallelogram-shaped structure, and wherein one of the longitudinal members is coupled to the proximal ring and the other longitudinal member is coupled to the distal ring.

11. An apparatus for exploration or treatment of a vessel or organ, the apparatus comprising:
- a flexible elongated body having a proximal end and a distal extremity, the distal extremity including an ablation end effector having irrigation ports;
- at least one irrigation channel disposed within the flexible elongated body, the at least one irrigation channel being in fluid communication with the irrigation ports;
- a force measurement structure affixed to the distal extremity of the flexible elongate body, the force measurement structure including a proximal ring and a distal ring separated by a flexible structure, the proximal and distal rings being arranged concentrically about a longitudinal axis, the force measurement structure being operatively coupled with an emitter and a plurality of receivers, the plurality of receivers adapted to receive signals emitted from the emitter and, in response, the plurality of receivers adapted to output signals that vary in response to a displacement of the distal ring relative to the proximal ring due to a contact force on an exterior of the distal extremity of the flexible elongate body; and
- a controller including a microprocessor operatively coupled with the plurality of receivers and adapted to receive and process the signals output therefrom, the microprocessor being configured to compute a contact force vector from the signals, the contact force vector being multi-dimensional and corresponding to the contact force on the exterior of the distal extremity of the flexible elongate body.

12. The apparatus of claim 11, wherein the controller is configured to control operation of the ablation end effector based on the signals output from the plurality of receivers.

13. The apparatus of claim 12 wherein the controller is configured to operate the ablation end effector when a magnitude of the multi-dimensional force is within a predetermined range of values.

14. The apparatus of claim 11 wherein the proximal ring is continuous and the distal ring is continuous.

15. The apparatus of claim 11 wherein the proximal ring, the distal ring and the flexible structure are integrally formed.

* * * * *